(12) United States Patent
Hörth et al.

(10) Patent No.: US 6,500,001 B2
(45) Date of Patent: *Dec. 31, 2002

(54) DEVICE FOR DISPENSING MULTI-COMPONENT COMPOUNDS FOR DENTAL PURPOSES

(75) Inventors: Hans Hörth, Hamburg (DE); Hans-Dieter Höhnk, Reinbek (DE); Andreas Iburg, Hamburg (DE)

(73) Assignee: Ernst Muhlbauer KG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/545,152

(22) Filed: Apr. 7, 2000

(65) Prior Publication Data

US 2002/0064754 A1 May 30, 2002

(30) Foreign Application Priority Data

Apr. 9, 1999 (DE) .................................... 299 06 343 U

(51) Int. Cl.$^7$ ................................................ A61C 5/04
(52) U.S. Cl. .............................. 433/89; 433/80; 433/90
(58) Field of Search ............................. 433/80, 81, 89, 433/90

(56) References Cited

U.S. PATENT DOCUMENTS

| | | | | | |
|---|---|---|---|---|---|
| 4,153,403 A | * | 5/1979 | Schneider | ................... | 425/159 |
| 4,184,776 A | * | 1/1980 | Shampanier | ................ | 366/198 |
| 4,704,088 A | * | 11/1987 | Newman | ..................... | 433/81 |
| 4,826,431 A | * | 5/1989 | Fujimura et al. | .......... | 433/215 |
| 4,905,526 A | * | 3/1990 | Magnussen, Jr. et al. | | 73/864.18 |
| 5,405,614 A | * | 4/1995 | D'Angelo et al. | .......... | 424/449 |
| 5,525,058 A | * | 6/1996 | Gallant et al. | ................ | 433/88 |
| 6,048,201 A | * | 4/2000 | Zwingenberger | ............ | 433/90 |

* cited by examiner

Primary Examiner—John J. Wilson
(74) Attorney, Agent, or Firm—Alix, Yale & Ristas, LLP

(57) ABSTRACT

Device for dispensing multi-component compounds, in particular for dental purposes. It is equipped with a timer for indicating one or more times which are relevant to the working of the compound. This timer can be triggered by the start and/or the end of the running of the device.

18 Claims, 1 Drawing Sheet

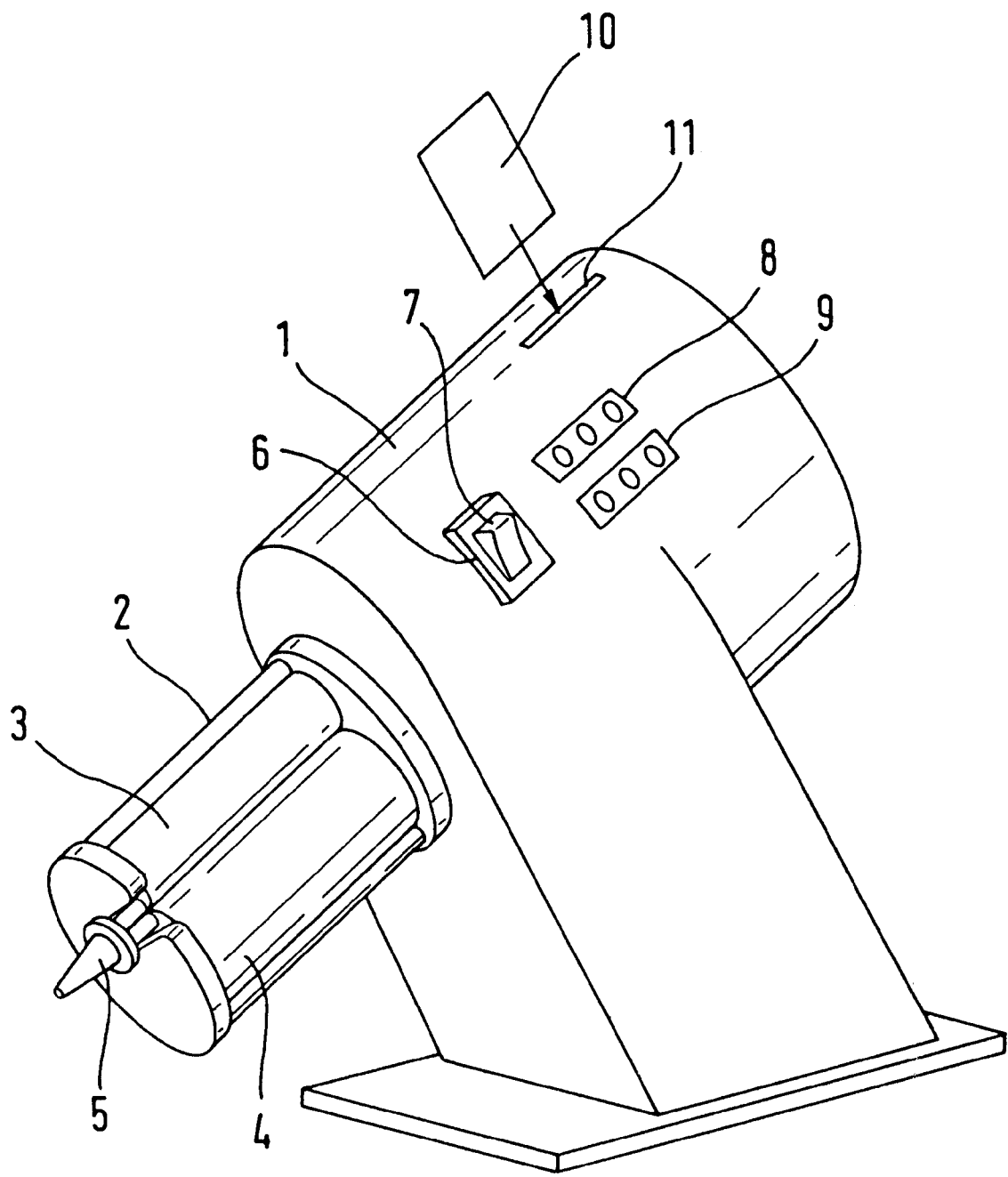

DEVICE FOR DISPENSING MULTI-COMPONENT COMPOUNDS FOR DENTAL PURPOSES

Devices for mixing and dispensing multi-component compounds for dental purposes, for example as impression compound, are known. Since the reaction of the components begins with the mixing, there is only a limited working time available after the start of dispensing of the compound. An impression compound, for example, must be placed in the mouth before the working time has expired. The second important time for the dentist is the hardening time. In the case of an impression compound, this is the time it is necessary to wait before the material can be removed from the mouth. Although experience does give the dentist some feel for the length of time the compound can be worked and for when the material has completely set, mistakes regarding the time interval that has elapsed are still possible, especially in the case of complex impressions, and these mistakes can lead to incorrect results, for example poorly fitting impressions, and consequently to unnecessary expenditure in terms of time and cost. The same applies to other applications. For example, when preparing temporary crowns or bridges, it is necessary to observe the gelling time in which the mixed compound is in an elastic phase and can thus still be removed from the undercut tooth stump. The invention affords the user a means giving more precise information regarding the times available to him. According to the invention, a timer for indicating times which are to be observed is connected to the device for dispensing multi-component compound.

A particularly advantageous embodiment of the invention is one in which the timer is automatically triggered as a function of the running of the dispensing device. This preferably occurs at the start and/or at the end of the delivery procedure. If the working time is to be displayed, i.e. the length of time which at each point in time is still available for working the material, the timer runs from the start of the delivery procedure. If the hardening time is to be displayed, i.e. the length of time after which the last-applied material has also hardened, the timer runs from the end of the delivery procedure. Since the delivery time can vary greatly between different working techniques, the two time intervals can be differently staggered in relation to each other. For example, the movement of a switch, with which the dispensing device is started up, can simultaneously start the timer for the working time. Correspondingly, using the switch with which the dispensing is ended, a second timer can be started up which displays the hardening time.

As regards the way in which the timer signals the time, recourse may be had to known display possibilities. For example, the time still remaining at each point in time until expiry of the working time or hardening time can be displayed in seconds or minutes. Alternatively, the length of time which has elapsed since the timer was started is displayed. Since the dentist should have the possibility of controlling the preset time interval in each case and of adjusting his work thereto, this time interval should be displayed before the delivery procedure has commenced. In many cases, one signal is sufficient for displaying the end of the set time, for example the working time or the hardening time. If the time concerned is one where it is necessary to do something before the said time has expired (working time, gelling time), the signal is given before the time has expired, so that the dentist still has time to act, or a preliminary signal is given before the signal which indicates the time has expired. If, by contrast, the expiry itself is relevant, only this need be signalled. The signal can be an acoustic one, for example, so that the dentist can give his full visual attention to the patient. The timer is preferably reset automatically to the initial status, i.e. to the preset time interval, after the display. In another variant, the timer is reset automatically to the initial status on each newly commencing delivery procedure.

If only compounds are ever to be worked having about the same duration of the relevant time interval or time intervals, the respective display interval of the timer can be preset by the manufacturer such that it cannot be altered. Instead of this, it is also possible for the time interval of the timer to be set by the user for each case of use. A further possibility is one in which although the time interval can be adjusted, the selected setting is stored so that it does not have to be selected again upon each use.

If compounds with different working, gelling and hardening times can be worked in one dispensing device, which compounds are fitted in the device in the form of exchangeable cartridges, it is particularly advantageous for the exchangeable cartridges and the device or the timer to be provided with interacting facilities for automatically setting the time interval to be given to the timer. To do this, it is possible, for example, to use the technique which is known for automatically setting the film sensitivity in cameras. The device is equipped with a facility for reading a bar code, punched code, color code or magnetic strip code provided on the cartridge. The code can be applied directly on the cartridge and can also be read directly from there. However, it is also possible to provide the code separately from the cartridge or container holding the material and to read the code at another point on the device. For example, it can be arranged on a packaging or on a control chip which is enclosed with the package and which delivers the desired control commands for the timer. With the code or with the chip, in whichever form it may be provided, other material-dependent functions of the device can also be controlled, for example the mixing speed, the delivery speed or the dispensing quantity. The latter, for example, can be predetermined by the timer as a function of the dispensing time. The automatic presetting of the display of the working time or hardening time should be able to be manually overridden in order to allow the user to adapt to different working conditions.

With reference to the drawing, the body 1 thereof bears a holder 2 for exchangeable cartridges 3, 4, the outlets of which are connected to a mixing nozzle 5. The device 1 contains pistons which from the rear side are driven into the cartridges 3, 4 in order to expel the components therefrom into the nozzle 5 from which the mixed components are extruded.

The device 1 has an electronic control circuit 6 with a switch 7. The electronic circuit includes also the timers. There are displays 8, 9 which show the time period (for instance in seconds) which the timers are adjusted to. During the operation they show the time still available before the end of the respective time period. for instance, the display 8 shows the working time and display 9 the hardening time.

If, for example, the working time for a mixture of the components in the cartridges 3, 4 is "x" and thereafter a hardening time of "y" is to be observed, a first timer in the electronic device 6 is adjusted to the working time and (before the start of the device) this time period "x" is shown by the display 8. The second timer of the electronic device 6 is adjusted to the hardening time "y" which before the start of the device is shown by display 9. If now the operator pushes the switch 7 and thereby starts the extrusion of the material out of the nozzle 5, also the first timer in the electronic device 6 is triggered. Device 8 now counts down until zero and shows the working time still available. After extrusion of the quantity desired, the dentist works the material, for instance, in order to make an impression in the mouth of a patient. Thereby he observes display 8 in order to be sure that he finishes the working before expiry of the working time period. When this period ends, the device 1 may generate an acoustic signal.

When the first timer and the display 8 shows the end of the working time, electronic device starts the second timer and display 9 to show the hardening time still to be waited. Alternatively, the second timer and display 9 could be triggered also when the button 7 is pushed. The display 9 tells the dentist the time period which the material should be kept in its position in the mouth of the patient before it can be removed therefrom. Again, the end of this period could be indicated by an acoustic signal.

The adjustment of the time periods can be done arbitrarily by means known for such purposes, for instance, in alarm clocks. Alternatively, there is provided a chip card 10 which accompanies the cartridges 3, 4 and which bears a code which after insertion into slot 11 can be read by the device for adjustment of the electronic circuit 6 and the timers thereof.

What is claimed is:

1. A device that mixes and extrudes multi-component dental compounds, said device comprising:
   a body;
   a facility on said body for supporting at least one exchangeable cartridge containing the components of the dental compound;
   a mixing nozzle adjacent said facility, said mixing nozzle configured to mix the components of the dental compound during extrusion of the compounds from the at least one cartridge;
   a timer supported by said body; and
   a display operatively connected to the timer to digitally indicate one or more time intervals relevant to the working of the multi-component dental compound being mixed and extruded.

2. The device of claim 1, wherein the timer is triggered by running of the device to extrude dental compound.

3. The device of claim 2, wherein the timer is triggered at the start of the running of the device.

4. The device of claim 3, wherein said time intervals comprise a time interval beginning with the start of the running of the device and a time interval beginning with the end of the running of the device.

5. The device of claim 2, wherein the timer is triggered at the end of the running of the device.

6. The device of claim 5, wherein said time intervals comprise a time interval beginning with the start of the running of the device and a time interval beginning with the end of the running of the device.

7. The device of claim 1, comprising a facility for automatically resetting the timer after it has run its course.

8. The device of claim 1, comprising a facility for automatically resetting the timer upon a new start-up of the device.

9. The device of claim 1, wherein a code carrier is assigned to the at least one exchangeable cartridge, and the device is equipped with a facility for scanning the code and for setting the timer according to the code.

10. The device as claimed in claim 9, wherein the code is designed also to predefine and set further operating parameters selected from the group consisting of mixing speed, delivery speed and dispensing quantity.

11. A method for dispensing multi-component compounds for dental purposes from a dispensing device having at least one timer, said method comprising:
    installing a plurality of components into the dispensing device;
    triggering the timer to begin counting upon initiation of dispensing;
    initiating dispensing of said compound from said device;
    working the dispensed compound;
    completing the dispensing of the compound from the device; and
    referring to said timer, wherein said timer displays the elapsed time from said initiating.

12. The method of claim 11, and further comprising triggering a second timer to begin counting upon completion of dispensing and the step of referring comprises said timer displaying the elapsed time from said completion.

13. The method of claim 12, wherein the method includes the preliminary step of:
    inputting into the device the hardening time of the compound to be dispensed;
    and the method further comprises said device generating a signal indicating the end of said hardening time.

14. The method of claim 13, wherein the step of installing comprises inserting a cartridge containing said plurality of components into said dispensing device and the step of inputting comprises the device reading said hardening time from said cartridge.

15. The method of claim 11, wherein the step of installing comprises inserting a cartridge containing said plurality of components into said dispensing device.

16. The method of claim 15, wherein the method includes the preliminary step of:
    inputting into the device the working time of the compound to be dispensed;
    and the method further comprises said device generating a signal as the end of said working time approaches.

17. The method of claim 16, wherein the step of inputting comprises the device reading said working time from said cartridge.

18. The method of claim 11, wherein said device comprises first and second timers and said method further comprises:
    setting said second timer to begin counting upon completion of dispensing, said second timer displaying the elapsed time from said completion; and
    inputting into the device the working time and hardening time of the compound, said device generating a first signal as the end of said working time approaches and a second signal indicating the end of said hardening time.

* * * * *